US00PP23793P2

(12) United States Plant Patent
Kordes

(10) Patent No.: US PP23,793 P2
(45) Date of Patent: Aug. 6, 2013

(54) MINIATURE ROSE PLANT NAMED 'KORPOT007'

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 44 days.

(21) Appl. No.: 13/385,354

(22) Filed: Feb. 14, 2012

(51) Int. Cl.
*A01H 5/00* (2006.01)

(52) U.S. Cl.
USPC ..... Plt./116

(58) Field of Classification Search
USPC ..... Plt./116
See application file for complete search history.

(56) References Cited

U.S. PATENT DOCUMENTS

PP7,058 P * 11/1989 Saville ..... Plt./116

OTHER PUBLICATIONS

Anonymous. "Kordana Potroses Special Miniature Roses" see p. 2. Available at http://www.kordes-rosen.com accessed May 20, 2013.*
Anonymous. "Greenheart Kordana" see p. 3. available at www.greenheartfarms.com accessed May 20, 2013.*

* cited by examiner

*Primary Examiner* — Wendy C Haas

(57) ABSTRACT

A new and distinct variety of rose having long lasting, novel yellow flowers with red petal margins and attractive foliage. The variety is suitable for forcing as a floral pot rose plant. The new variety has very good disease resistance. It exhibits uniform growth with abundant long lasting flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot007'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2006. The crossing was between an 'unnamed seedling' and an 'unnamed seedling' (both unpatented).

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot007'.

SUMMARY OF THE INVENTION

The new rose plant may be distinguished from its seed parent, an 'un-named seedling' by the following combination of characteristics:

1. 'KORpot007' has a good duration of flowers as a commercial pot rose while the seed parent has average duration of flowers as a commercial pot rose variety.

2. 'KORpot007' has a medium growth habit while the seed parent has a compact growth habit.

The new rose plant may be distinguished from its pollen parent, an 'un-named seedling' by the following combination of characteristics:

1. The general flower color of 'KORpot007' is yellow with a red petal edge while the flower of the pollen parent is cream white.
2. The growth habit of 'KORpot007' is moderately compact while the growth habit of the pollen parent is upright and tall.

The objective of the hybridization was to create a new and distinct rose plant with unique qualities, such as:

1. Uniform growth and flowering;
2. Abundant yellow attractive, recurrent flowers;
3. Attractive and abundant foliage; and
3. Excellent shelf life for the plant when grown as a commercial pot rose.

This combination of qualities is not present in prior rose cultivars known to the inventor. These objectives have been substantially achieved and in that distinguish 'KORpot007' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot007' was selected in May 2007 from the seedling beds to be asexually propagated for further evaluation. The first asexual propagation of 'KORpot007' was done in May, 2007 by taking and rooting cuttings at the inventor's nursery in Offenseth-Sparrieshoop, Germany.

This initial and other subsequent propagations conducted in controlled environments demonstrate that 'KORpot007' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, petals, prickles, and stems of 'KORpot007'.

DETAILED BOTANICAL DESCRIPTION

The following is a description of 'KORpot007', as observed growing in October, 2011 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORspunty', a rose variety from the same inventor described and illustrated in U.S. Plant Pat. No. 17,402 and issued on Feb. 6, 2007 are compared to 'KORpot007' in Chart 1.

CHART 1

| Characteristic | 'KORpot007' | 'KORspunty |
|---|---|---|
| Bud Color as sepal unfold. | Yellow Group 14D with petal margin Red Group 45B. | Yellow Group. 9A |
| Sepal Size. | 20-25 mm long and 6-8 mm wide. | 30-35 mm long and 8-10 mm wide. |
| Petal Count | Double 38-40 petals | Very Double 50-60 petals. |

Parents:

*Seed parent.*—'Unnamed seedling'.

*Pollen parent.*—'Unnamed seedling'.

Classification:

*Botanical classification.*—*Rosa hybrida* 'KORpot007'.

*Commercial classification.*—Miniature rose.

FLOWER AND FLOWER BUD

Blooming habit: Recurrent.

Flower bud:

*Size.*—Upon opening, 18 mm in length from base of receptacle to distal end of bud and 12 mm diameter at its widest point.

*Bud form.*—Short, pointed ovoid.

*Bud color.*—As sepals first unfold, bud color is Yellow Group 14D with the petal margin being Red Group 45B. When ¼ open, the upper surface of petals is Yellow Group 14B, and the lower surface is Yellow Group 14D with intonation of Red Group 46A on petal margin.

*Sepals.*—Color: Upper surface Yellow-Green Group 146C. Lower surface Yellow-Green Group 146C. Size: Average 20-25 mm (l)×6-8 mm (w). Shape: Weak foliaceous appendages on two of the five sepals. Apex: Appiculate. Base: Flat at union with receptacle. Quantity: Five. Surface texture: Upper side: Lightly pubescent. Lower surface: Glaborous. Margins: Stipitate glands are present on the margins.

Receptacle:

*Surface.*—Smooth.

*Color.*—Yellow-Green Group 144B.

*Shape.*—Funnel.

*Size.*—10 mm (h)×7 mm (w).

Peduncle:

*Surface.*—With fine hairs and stipitate glands.

*Length.*—40 to 50 mm average length.

*Diameter.*—2 to 3 mm average diameter.

*Color.*—Yellow-Green Group 144A.

*Strength.*—Strong.

*Borne.*—Singularly.

Flower bloom:

*Fragrance.*—None.

*Duration.*—On the plant 14 to 16 days, long lasting. As a cut flower, 8 to 10 days. Senesced petals clinging.

*Size.*—Medium for a miniature rose. When open, the average flower diameter is 50 mm and the average flower height is 18 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Basal portion of the petal is Yellow Group 13C. The marginal and middle zones of the petal are Red Group 53A and Red Group 53B. Inner Side: Yellow Group 13A with margins of the petal having intonations of Red Group 45A. Innermost petals: Outer Side: Yellow Group 13A. Inner Side: Yellow Group 13A.

*Upon opening, basal petal spots.*—Basal petal spot, outermost petals: Outer Side: Green-Yellow Group 1A. Inner Side: Green-Yellow Group 1B. Basal petal spot, innermost petals: Outer Side: No distinctive basal petal spot. Inner Side: No distinctive basal petal spot.

*After opening, petals.*—Outermost petals: Outer Side: Yellow-Orange Group 16B with intonations of Red Group 44B on the middle and marginal zones of the petals. Inner Side: Yellow Group 16B with intonations of Red Group 44B on petal margins. Innermost petals: Outer Side: Yellow-Orange Group 14B with intonations of Red Group 45C on petal margins. Inner Side: Yellow Group 12A with intonations of Red Group 40C on petal margins.

*After opening, basal petal spots.*—Basal petal spot, outermost petals: Outer Side: Green-Yellow Group 1A. Inner Side: No distinctive coloration at petal base observed. Basal petal spot, innermost petals: Outer Side: No distinctive coloration at petal base observed. Inner Side: No distinctive coloration at petal base observed.

General tonality: On open flower: Yellow Group 13A with intonations of Orange-Red Group 34A. No change in the general tonality at the end of the eighth day. Afterwards, general tonality is Orange-Red Group 23C with intonations of Red Group 43C.

Petals:

*Petal count.*—Double.

*Average range.*—Approximately 38-40 petals under normal conditions.

*Petal reflex.*—Petals reflex strongly.

*Petal edge.*—Entire.

*Petal shape.*—Obovate. Apex shape is obtuse. Shape of base is deltoid.

*Petal size.*—15 mm (l)×15 mm (w).
*Thickness.*—Average.
*Petal arrangement.*—Formal.

Petaloids:
*Petaloid count.*—Average of 10-14 per flower.
*Petaloid size.*—Petaloids are 8-10 mm (l) and 3-5 mm (w).
*Petaloid color.*—Color of inner side is Yellow Group 13A with intonations of Red Group 40B on the margins. Color of outer side is Yellow Group 13B with intonations of Red Group 40B on the petal margins.
*Petaloid texture.*—Thin.
*Margins.*—Undulated.
*Petaloid shape.*—Most commonly deltoid, with some petaloids highly irregular. Apex: Obtuse. Base: Attenuate.

Reproductive organs:
*Pistils.*—Average number of pistils: Approximately 12. Stigmas: Location: Slightly superior in position to anthers. Color: Greyed-Yellow Group 161D. Styles: Length: About 4 mm long. Color: Greyed-Yellow Group 161B with intonations of Greyed-Red 180D.
*Stamens.*—Approximately 30 on average and regularly arranged. Anthers: Size: Average length was approximately 1 mm. Pollen: Generally present. Color: Greyed-Orange Group 164B. Filaments: Color: Yellow Group 14C with intonations of Red Group 46B. Length: 5 mm.

THE PLANT

Growth: Moderate growth.

Plant habit: Compact and upright. When grown as a 14 cm container plant the average plant height is 18 cm and the average plant width is 14 cm.

Stems:
*Stem color.*—Young wood: Yellow-Green Group 144A. Older wood: Yellow-Green Group 144A.
*Stem surface.*—Young wood: Smooth. Older wood: Smooth.

Prickles: Present.
*Incidence.*—Average of 4 per each 10 cm of stem.
*Size.*—Average length: 7 mm.
*Color.*—Immature prickles: Yellow-Green 145C. Mature prickles: Yellow Green 145C.
*Shape.*—Linear.
*Anthocyanin.*—Immature prickles with intonations of Greyed-Red 181C.

Leaves and leaflets: Normally 5 leaflets on normal leaves in middle of the stem.
*Venation pattern.*—Pyramidal net pattern.
*Leaf size.*—9 mm (l)×7 mm (w).
*Abundance.*—Average.
*Texture.*—Thin. Upper side of leaflet smooth and glossy. Under side of leaflet: Matte and smooth.
*Color, mature foliage.*—Upper Leaf Surface: Green Group 137A. Lower Leaf Surface: Green Group 137C.
*Color, juvenile foliage.*—Upper Leaf Surface: Green Group 137B. Lower Leaf Surface: Green Group 137C.
*Anthocyanin intonation.*—Present. Intonations of Greyed-Red Group 182A were present on juvenile leaf margins, veins, and undersides of juvenile foliage.

Stipules:
*Size.*—8 mm long, 4 mm from distal tip to distal tip.
*Stipule color.*—Yellow-Green Group 146C.
*Anthocyanin.*—Greyed-Red Group 181C on immature stipules.
*Margins.*—Stipitate glands present.
*Shape.*—Apex: Apiculate. Base: Flat.

Petiole:
*Length.*—Average 14 mm.
*Diameter.*—Average 2 mm.
*Petiole color.*—Yellow Green Group 146B.
*Underneath.*—Smooth with an occasional prickle.
*Margins.*—With stipitate glands.
*Anthocyanin.*—Greyed-Red Group 181B on juvenile foliage.

Petiole rachis:
*Length.*—Average 18 mm.
*Diameter.*—Average 2 mm.
*Color.*—Yellow-Green Group 146C. Anthocyanin present on upper side of juvenile and mature foliage: Greyed-Red Group 183B.

Prickles: A few small prickles underneath.

Stipitate glands: Limited numbers of stipitate glands on margins and underside.

Leaflets:
*Size.*—Average size of the terminal leaflet is 40 mm (l)×20 mm (w).
*Shape.*—Ovate. Base: Obtuse. Apex: Acute.
*Margins.*—Finely serrated.
*Surface.*—Upper: Glossy. Underneath: Matte.
*Texture.*—Thin.
*Arrangement.*—Odd pinnate.
*Venation.*—Reticulate.

Hips/seed formation: None observed.

Winter hardiness: Unknown.

Disease resistance: Very good resistance to Powdery mildew (*Sphaerotheca pannosa*) and *Botrytis* (*Botrytis cinerea*) diseases under normal growing conditions.

I claim:

1. A new and distinct variety of rose plant, as described and illustrated herein.

* * * * *

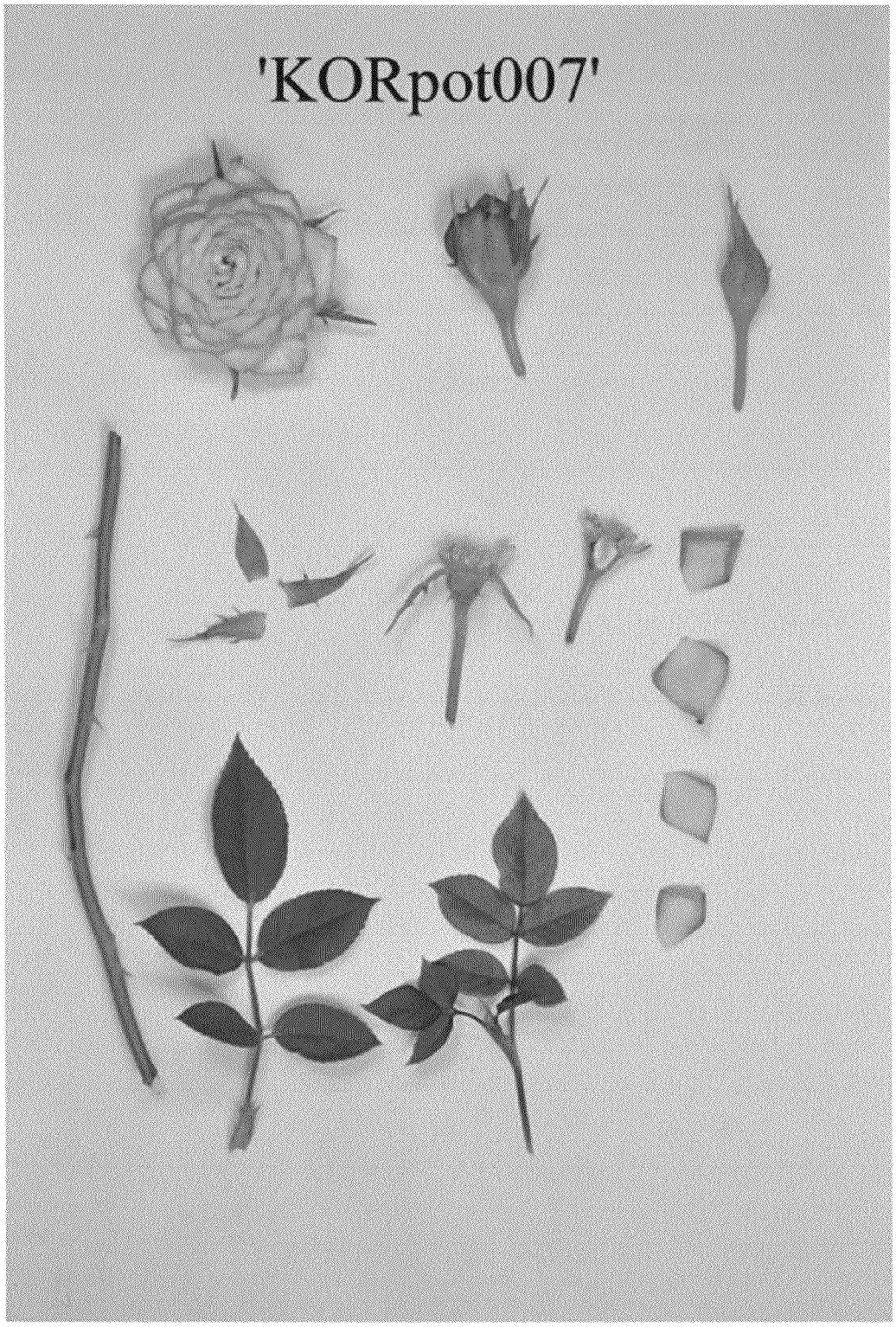
'KORpot007'